Nov. 17, 1964 G. L. THOMAS, JR Plant Pat. 2,453
WATER LILY PLANT
Filed Nov. 1, 1963
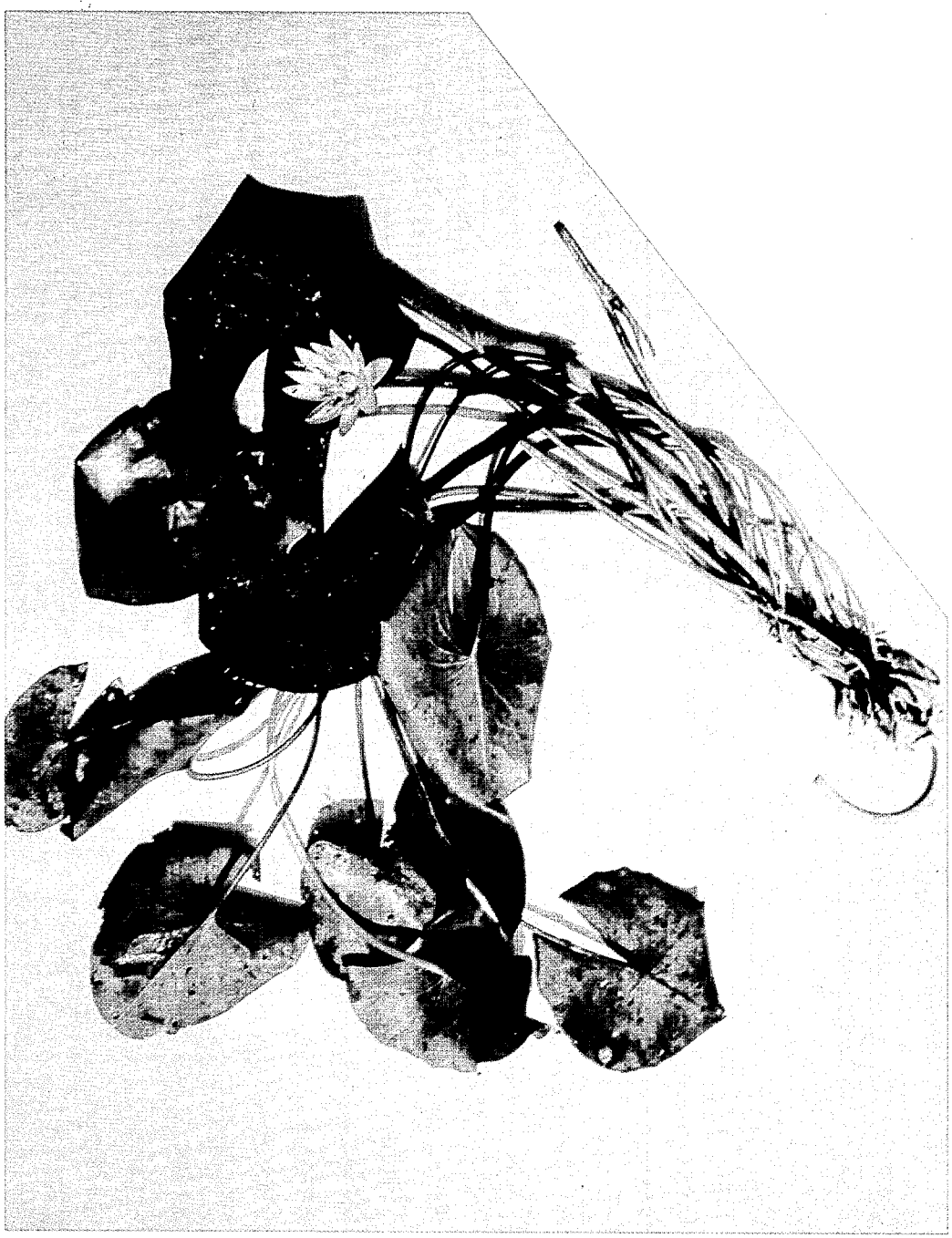
Inventor.
George L. Thomas, Jr.
By: Robb & Robb
Attorneys United States Patent Office Plant Pat. 2,453

Patented Nov. 17, 1964

2,453

WATER LILY PLANT

George L. Thomas, Jr., Lilypons, Md.

Filed Nov. 1, 1963, Ser. No. 320,975
1 Claim. (Cl. Plt.—68)

The present invention relates to a new and distinct variety of tropical water lily plant, which was originated by me by crossing the variety known as "Dauben" (unpatented) with the variety known as "August Koch" (unpatented).

As the result of this breeding, I have produced a new variety of water lily plant, which is unique and distinct from all other varieties of which I am aware, as evidenced by the following combination of outstanding characteristics which are present in the new variety:

(1) Suitability for growing and blooming in aquariums, and being superior in this respect to all other varieties known to me;

(2) A small, dwarf-like size;

(3) Distinctive and attractive Light Blue flowers which have fewer petals than other regular tropical water lilies;

(4) Long-lasting qualities;

(5) A viviparous habit; and (6) Excellent shipping qualities.

The parent variety "Dauben" is noted for its small size and suitability for tub culture. It bears well-shaped blooms of pale Lavender Blue color, which have a pronounced sweet fragrance. This variety is also very viviparous, but is not suitable for breeding in aquariums.

The parent variety "August Koch" is most noted for its large, pale Wisteria-Violet blooms which have Reddish Yellow stamens, and the blooms are profuse and fragrant. However, here again, the variety is not suitable for culture in aquariums, contrary to the new variety disclosed herein.

Asexual reproduction of my new water lily plant by viviparous shoots originating in the center of mature leaves, and also by tuber-like divisions which form under the crown of the plant, as performed by me at Lilypons, Maryland, shows that the foregoing characteristics and distinctions are fixed and come true, and are transmissible through succeeding propagations.

The accompanying drawing shows typical specimens of the flowers and foliage, as well as the root system, of my new variety in different stages of development and as depicted in color as nearly true as it is reasonably possible to make the same in a color illustration of this character, with both the upper and under surfaces of the main leaves being depicted. However, the illustrated blossom has not quite achieved its mature, Light Blue color.

The following is a detailed description of my new water lily plant, as based upon observations of specimens grown at Lilypons, Maryland, with color terminology in accordance with the Nickerson Color Fan, except where general color terms of ordinary dictionary significance are obvious:

Parentage: Seedling of "Dauben"×"August Koch."

Propagation: Holds its distinguishing characteristics through succeeding propagations by viviparous shoots and by tuber-like root divisions.

*Plant*

Foliage:

*Submerged leaves.* — Shape — arrowhead. Length (from petiole to sinus)—1½ inches. Color: upper side—Moderate Yellow Green, Plate 2.5GY 5/5; under side—Light live, Plate 7.5Y 5/5.

*Main floating leaves.* — Shape — basically round. Length (from petiole to sinus)—2 inches. Color—Moderate Yellow Green, Plate 7.5GY 5/7.

*Mature leaves.*—Shape—basically round. Size—2½ inches. Color: upper side—Moderate Olive Green, Plate 7.5GY 4/4; under side—Strong Yellow Green, Plate 5GY 6/8.

*Leaf stem.*—Color—Moderate Pink, Plate 5R 8/6 near the base, with remainder of stem Strong Yellowish Brown, Plate 7.5YR 5/7 blended with Pale Orange Yellow, Plate 7.5YR 9/4. Length—varies according to water depth.

*Flower*

Bloom:

*Habit.*—Continuous.

*Size.*—About 3 inches if flower is manually spread to maximum diameter.

*Color.*—Light Blue, Plate 10B 7/6.

*Number of days open.*—4 to 5.

*Fragrance.*—Sweet.

*Number open at one time.*—From 1 to 3.

*Distance standing out of water.*—Floating, or up to 1 inch above water.

Buds:

*Shape.*—Normal water lily shape; pointed.

*Color.*—Strong Yellow Green, Plate 7.5GY 6/8.

Scape:

*Color.*—Light Yellowish Pink, Plate 7.5R 9/3.

*Height above water.*—¼ inch.

*Ridges.*—None.

Sepals:

*Number.*—4.

*Color.*—Strong Yellowish Green, Plate 7.5GY 6/8.

*Length.*—1½ inches.

*Width.*—½ inch.

*Shape.*—Characteristic water lily shape; pointed.

*Texture.*—Similar to that of parent variety "Dauben."

Petals:

*Number.*—14.

*Shape.*—Long; narrow; slightly curved in characteristic fashion of pointed shaped water lilies.

*Length.*—1⅜ inches.

*Width.*—5/16 inch.

*Color.*—Light Blue, Plate 10B 7/6.

Stamens:

*Number.*—76.

*Length.*—Outer—¾ inch.
Inner—9/16 inch.

*Appendages.*—With.

*Shape.*—Characteristic shape for pointed water lilies.

Carpels:

*Number.*—16.

*Length.*—⅛ inch.

*Color.*—Brilliant Greenish Yellow, Plate 7.5Y 9/8.

Stigma: Color—Vivid Greenish Yellow, Plate 7.5Y 8/12.

Receptive: Yes.

Lasting quality: Very good.

Shipping quality: Excellent.

*Fruit*

Shape: Spherical.

Size: ¼ inch in diameter.

Seeds: Present; fertile.

I claim:

A new and distinct variety of tropical water lily plant, substantially as herein shown and described, characterized particularly as to novelty by the unique combination of superior suitability for growth and blooming in aquariums, a small, dwarf-like size, distinctive and attractive Light Blue flowers which have fewer petals than regular tropical water lilies, long-lasting flower qualities, excellent shipping qualities, and a distinctive viviparous habit.

No references cited.